US009377460B2

(12) United States Patent
Lalvani

(10) Patent No.: US 9,377,460 B2
(45) Date of Patent: Jun. 28, 2016

(54) DIAGNOSTIC MYCOBACTERIUM TUBERCULOSIS TEST

(76) Inventor: Ajit Lalvani, Oxford (GB)

( * ) Notice: Subject to any disclaimer, the term of this patent is extended or adjusted under 35 U.S.C. 154(b) by 152 days.

(21) Appl. No.: 13/263,442

(22) PCT Filed: Apr. 9, 2010

(86) PCT No.: PCT/EP2010/054721
§ 371 (c)(1),
(2), (4) Date: Feb. 7, 2012

(87) PCT Pub. No.: WO2010/115989
PCT Pub. Date: Oct. 14, 2010

(65) Prior Publication Data
US 2012/0128708 A1 May 24, 2012

(30) Foreign Application Priority Data

Apr. 9, 2009 (GB) .................................. 0906215.9

(51) Int. Cl.
*A61K 39/04* (2006.01)
*A61K 39/00* (2006.01)
*G01N 33/53* (2006.01)
*G01N 33/569* (2006.01)
*G01N 33/50* (2006.01)

(52) U.S. Cl.
CPC .......... *G01N 33/5695* (2013.01); *G01N 33/505* (2013.01)

(58) Field of Classification Search
USPC .................. 424/9.1, 9.2, 184.1, 185.1, 234.1, 424/248.1; 435/4, 7.1, 7.2; 530/300, 350
See application file for complete search history.

(56) References Cited

FOREIGN PATENT DOCUMENTS

| EP | 0 693 119 | 10/1994 |
|---|---|---|
| WO | WO 02/074903 | 9/2002 |
| WO | WO 2008/028489 | 3/2008 |
| WO | WO 2009/024822 | 2/2009 |
| WO | WO 2009/060184 | 5/2009 |
| WO | WO-2010121618 A1 | 10/2010 |

OTHER PUBLICATIONS

Arend et al., "Detection of active tuberculosis infection by T cell responses to early-secreted antigenic target 6-kDa protein and culture filtrate protein 10," *Journal Infectious Diseases*, 181:1850-1854, 2000.
Buddle et al., "Identification of immune response correlates for protection against bovine tuberculosis," *Veterinary Immunology and Immunopathology*, 108:45-51, 2005.
Chapman et al., "Rapid detection of active and latent tuberculosis infection in HIV-positive individuals by enumeration of *Mycobacterium tuberculosis*-specific T cells," *AIDS*, 16:2285-2293, 2002.
Devereux et al., "A comprehensive set of sequence analysis programs for the VAX," *Nucleic Acids Research*, 12:387-395, 1984.
Dosanjh et al., "Improved diagnostic evaluation of suspected tuberculosis," *Ann Itern Med*, 148:325-336, 2008.
Lalvani et al., "Rapid effector function in CD8+memory T cells," *J. Exp. Med.*, 186:859-865, 1997.
Ota et al., "T-cell recognition of an immunodominant myelin basic protein epitope in multiple sclerosis," *Nature*, 346:183-187, 1990.
PCT International Preliminary Report on Patentability issued in International Application No. PCT/EP2010/054721, issued Oct. 11, 2011.
PCT International Search Report issued in International Application No. PCT/EP2010/054721, mailed Jul. 20, 2010.
Raghavan et al., "Secreted transcription factor controls *Mycobacterium tuberculosis* virulence," *Nature*, 454(7205):717-722, 2008.
Sidders et al., "Screening of highly expressed mycobacterial genes identifies Rv3615c as a useful differential diagnostic antigen for the *Mycobacterium tuberculosis* complex," *Infection and Immunity*, 76(9):3932-3939, 2008.
Response filed May 25, 2012 in reply to European Examination Report dated Apr. 24, 2013 entered during prosecution of related EP Appl. No. 10716313.1.
European Examination Report mailed Apr. 24, 2013 during prosecution of related EP Appl. No. 10716313.1
Response filed Nov. 1, 2013 in reply to European Examination Report dated Apr. 24, 2013 entered during prosecution of related EP Appl. No. 10716313.1
European Examination Report mailed Nov. 21, 2013 during prosecution of related EP Appl. No. 10716313.1
Response filed May 22, 2014 in reply to European Examination Report dated Nov. 21, 2013 entered during prosecution of related EP Appl. No. 10716313.1
European Examination Report mailed Jun. 16, 2014 during prosecution of related EP Appl. No. 10716313.1
Bercovici et al, "New Methods for Assessing T-Cell Responses", Clinical and Diagnostic Laboratory Immunology, 2000, pp. 859-864.
Deng et al, "Recognition of self-peptide-MHC complexes by autoimmune T-cell receptors", Trends in Biochemical Sciences, vol. 32, No. 11, pp. 500-508.
European Patent Office Communication pursuant to Rule 114(2) EPC, Third Party Observations in connection with related European Patent Application No. 10716313.1, dated Jul. 20, 2015, 6 pages.
Godfrey et al, "The Fidelity, Occasional Promiscuity, and Versatility of T Cell Receptor Recognition", Immunity, No. 28, 2008, pp. 304-314.
Klenerman et al, "Tracking T Cells With Tetramers: New Tales From New Tools", Nature Reviews, Immunology, vol. 2, 2002, pp. 263-272.

*Primary Examiner* — Rodney P Swartz
(74) *Attorney, Agent, or Firm* — Norton Rose Fulbright US LLP

(57) ABSTRACT

A method of diagnosing *Mycobacterium tuberculosis* infection in a human, or of determining whether a human has been exposed to *Mycobacterium tuberculosis*, comprising (i) contacting T-cells from said human with one or more of (a) a peptide having the sequence shown in SEQ ID NO 20, (b) a peptide having or comprising the sequence of at least 8 consecutive amino acids of the sequence shown in SEQ. ID NO 20; or (c) a peptide having or comprising a sequence which is capable of binding to a T-cell receptor which recognizes a peptide as defined in (a) or (b); and (ii) determining whether any of the said T-cells recognize said peptide, wherein steps (i) and (ii) are optionally carried out in vitro. The peptide is the product of the RV3615c gene.

21 Claims, 5 Drawing Sheets

DIAGNOSTIC MYCOBACTERIUM TUBERCULOSIS TEST

This application claims priority to PCT International Application Serial No. PCT/EP2010/054721, filed Apr. 9, 2010, and to GB Patent Application Serial No. 0906215.9, filed Apr. 9, 2009, both of which applications are incorporated by reference herein in their entirety.

FIELD OF THE INVENTION

The invention relates to a method of diagnosis of *Mycobacterium tuberculosis* (*M. tb*) infection in a human. It also relates to peptide compositions and a kit which can be used to carry out the diagnostic method. It also relates to vaccines and methods of vaccinating against *M. tb*.

BACKGROUND TO THE INVENTION

Accurate diagnosis of tuberculosis infection is essential for the treatment, prevention and control of this resurgent disease. Since *Mycobacterium tuberculosis* (*M. tb*) is often difficult to identify in patients with active tuberculosis, and impossible to directly identify in healthy latently infected people, an immune-based diagnostic test indicating the presence or absence of *M. tb* infection is useful for diagnostic evaluation of active tuberculosis and diagnosis and screening of latent *M. tb* infection.

The first measure of the cellular immune response to be exploited as a marker of *M. tb* infection, developed at the end of the $19^{th}$ century, was the tuberculin skin test (TST), which measures a delayed type hypersensitivity response to tuberculin purified protein derivative (PPD). This test has many drawbacks including poor specificity because of cross-reactivity of PPD, a crude mixture of over two hundred *M. tb* proteins widely shared between *M. tb* and *M. bovis* Bacille Calmette-Guerin (BCG) and most environmental mycobacteria. Hence false-positive results are common in people with environmental mycobacterial exposure and previous BCG vaccination. This presents a significant problem because most of the world's population is BCG-vaccinated and the confounding effect of BCG persists for up to 15 years after vaccination.

Comparative genomics has identified several genetic regions in *M. tb* and *M. bovis* that are deleted in *M. bovis* BCG. Several regions of difference, designated RD1 to RD16, between *M. tb* or *M. bovis* and BCG have been identified. All represent parts of the *M. bovis* genome deleted during prolonged in vitro culture. RD1 was deleted before 1921, when BCG was first disseminated internationally for use as a vaccine. RD1 is thus absent from all vaccine strains of BCG, as well as most environmental mycobacteria, but is still present in *M. tb* complex, including all clinical isolates of *M. tb* and *M. bovis*. There are nine open reading frames (ORFs) in the RD1 gene region. Early secretory antigen target-6 (ESAT-6) and culture filtrate protein 10 (CFP10) are encoded in RD1 and have been intensively investigated in animal models and humans over the last few years. ESAT-6 and CFP-10 are the strongest targets of the cellular immune response in *M. tb*-infected mice, cattle and tuberculosis patients and contacts. They are therefore now used as the key antigens in interferon-gamma release-assays (IGRAs) which exploit the fact that interferon-gamma-secreting T cells specific for ESAT-6 and CFP-10 are commonly detected in *M. tb*-infected persons but almost never detected in BCG-vaccinated persons.

The development and validation of such T cell-based interferon-gamma release assays (IGRAs) over the last decade is the first major advance in diagnosis of tuberculosis infection since the development of the tuberculin skin test 100-years ago. Although diagnostic sensitivity of commercially available IGRAs is higher than TST, their real-life clinical use demands higher sensitivity to enable rapid exclusion of active tuberculosis and reliably diagnose latent tuberculosis in those at highest risk of progression to tuberculosis and who are at risk of false-negative IGRA results, ie people who are immunosuppressed by virtue of HIV-infection, concomitant chronic illness (eg end-stage renal failure, diabetes, immune-mediated inflammatory diseases) medication (eg corticosteroids, anti-TNF-alpha agents) or young age (children under 5-years and especially under 2-years of age). One approach is to increase diagnostic sensitivity by incorporating additional antigens that are strong targets of T cell responses in *M. tb*-infected persons but not in BCG-vaccinated persons.

The Rv3615c gene is situated outside the RD1 locus and encodes a 103 amino-acid protein of unknown function. However, Rv3615c protein has been identified as a critical component of the secretion pathway called the Snm (secretion in mycobacteria) system (MacGurn et al *Molecular Microbiology* 2005 57:1653) involved in secreting the virulence factors ESAT-6 and CFP-10. This protein is not in the RD1 locus (which is absent in all strains of BCG vaccine) and thus is not expected to be specific for *M. tuberculosis* infection in BCG-vaccinated persons. This antigen is also not expected to be a strong target of T cell responses because the strongest T cell antigens in *M. tb*-infected humans are all secreted antigens and there is no available data to indicate that Rv3615c is secreted by *M. tb*. Moreover, there is no available evidence to indicate that Rv3615c is a T cell target in *M. tb*-infected humans.

Bovine TB, caused by *Mycobacterium bovis* (*M. bovis*), a pathogenic *mycobacterium* closely related to *M. tb*, is a major problem in UK cattle herds and results in a great economic burden. All cattle that are presumed to have *M. bovis* infection on the basis of positive skin test results in response to bovine tuberculin [PPD-B] are slaughtered because they cannot be used for milk or beef production and, if they develop active TB, become infectious to other cattle in the herd. Because of the great economic burden caused by bovine TB, veterinary researchers are actively investigating T cell immune responses in *M. bovis*-infected cattle in order to develop effective cattle vaccines and cattle diagnostics for improved prevention and early detection of bovine TB. With these objectives, a research group at the Veterinary Laboratories Agency in the UK investigated cellular immune responses to a range of *M. bovis* proteins that are highly expressed at the mRNA level during in vitro culture. As part of a screen of over 100 antigens, they found 14 genes that were strongly expressed at the mRNA level (Sidders et al. *Infection and Immunity* 2008 vol 76 (9); 3932-3939). On screening these proteins for T cell responses in cattle with presumed *M. bovis* infection, they found that 4 were T cell antigens, since they were recognised by IFN-gamma-secreting T cells from the cattle. The 4 *M. bovis* antigens were Mb2107c, Mb3299, Mb3776c and Mb3645c, and they gave IFN-gamma responses in 2, 3, 5 and 11 cows respectively out of 30 cattle (with presumed *M. bovis* infection) tested (Sidders et al. *Infection and Immunity* 2008 vol 76 (9); 3932-3939). The corresponding genes in *M. tb* are: Rv2081c, Rv3271c, Rv3750c and Rv3615c respectively. The screening used 20mer peptides representing the sequences of these 4 gene products in 30 cattle presumed to be naturally infected with *M. bovis* (on the basis that they had positive skin test results in response to bovine tuberculin [PPD-B]) from herds known to have bovine tuberculosis (Sidders et al. *Infection and Immunity* 2008 vol 76 (9); 3932-3939). Control cattle comprised 10 uninfected cattle obtained from herds in four yearly testing parishes with no history of bovine tuberculosis breakdown in the past 4 years (PPD-B skin test negative) and 20 cattle vaccinated with BCG Danish strain around 6 months prior to sampling. Although IFN-gamma responses to Mb3645c (Rv3615c) measured by whole blood ELISA were detected in 11/30 (37%) of the presumed *M. bovis*-infected cattle, no responses were detected to this antigen in either the naive (0/10) or BCG-vaccinated (0/20) cows. Responses to Mb3645c (Rv3615c) were identified in 4/7 *M. bovis*-infected cows that did not have interferon-gamma T cell responses to ESAT-6 and CFP-10. Thus, Mb3645c (Rv3615c) seems to be recognised by T cells from more cattle than the other 3 antigens, but this difference (11/30 vs 5/30) was not statistically significant (P=0.14, Fisher's exact test).

It is not possible to predict based on the antigen whether a T-cell antigen in cattle will also be a T-cell antigen in humans. There are a number of significant differences in antigen processing, presentation and recognition between cattle and humans. In addition, cattle have substantially different MHC molecules from humans, and are thus expected to recognise different antigens. Moreover, cattle are genetically more homogenous than out-bred human populations which are ethnically diverse and genetically heterogeneous. Accordingly, the skilled person would have no reason to consider a cattle antigen could be a T-cell antigen in other species.

As well as improving methods of diagnosis of *M. tb*, it would be useful to provide additional vaccines for *M. tb*. Although the immune mechanisms of protection against tuberculosis remain hitherto undefined, T cell-mediated immunity is essential for protection. All tuberculosis vaccine candidates currently in clinical trials (e.g. ESAT-6, MVA-85A, ESAT-6-Ag85B fusion molecule, recombinant BCG over-expressing 85A/Mtb10.4, Ad35 expressing 85A/85B/Mtb10.4) are based on *M. tuberculosis* antigens that elicit strong T-cell immunity during natural infection. A major challenge in vaccine development is to identify immunodominant antigens that elicit a strong IFN-gamma and IFN-gamma/IL-2 polyfunctional response from effector and memory T cells of both CD4 and CD8 T cell subsets. These vaccine antigens also need to be highly recognised in infected individuals across the human population to be immunogenic and effective in genetically heterogeneous out-bred populations.

SUMMARY OF INVENTION

The present invention identifies Rv3615c as one of the 3 most potent *M. tuberculosis* T-cell antigens in humans. We studied a cohort of 47 active tuberculosis patients, of whom 25 were culture-confirmed and 22 were highly probable tuberculosis, 23 latently infected subjects (latent TB infection=LTBI) and 31 healthy BCG-vaccinated controls with no known tuberculosis exposure (Tables 1 and 2). The mean age range of the tuberculosis patients was 35 years (range 18 to 79) of whom 20 were female. 37/43 patients had a BCG scar. The mean age range of the controls was 33 years (range 21 to 80) of whom 20 were female.

Remarkably, a very high proportion of tuberculosis patients had circulating IFN-gamma-secreting T cells specific for Rv3615c. 34/47 (72%) of tuberculosis patients responded to peptides from Rv3615c. Rv3615c potency was similar to ESAT-6 and CFP-10: 34/47 (72%) of tuberculosis patients responded to ESAT-6 and 35/47 (74%) responded to CFP-10 (Table 2). Potency to ESAT-6 and CFP-10 observed in our cohort is similar to published work [Arend et al Journal Infectious Diseases 2000 181: 1850; Chapman et al AIDS 2002 16:2285]. Crucially only 2/31 (6%) BCG-vaccinated donors responded to peptides from Rv3615c. These results indicate that Rv3615c has similar diagnostic sensitivity and specificity to ESAT-6 and CFP-10, making it one of the three most immunodominant *M. tb* antigens in TB-infected humans.

23 persons infected with latent tuberculosis infection were also studied. 14/23 LTBI subjects responded to Rv3615c peptides compared with 12/23 and 15/23 for ESAT-6 and CFP-10 respectively (Table 2). Significantly, the inventors identified 2/7 (29%) individuals responded to Rv3615c peptides but not to any of the 35 overlapping 15mer peptides spanning the length of ESAT-6 and CFP-10 (which are known to be immunodominant *M. tb* antigens of diagnostic utility). This result shows that Rv3615c peptides can be used to increase the sensitivity of diagnostic tests which use ESAT-6 and CFP-10 peptides for diagnosis of LTBI, without compromising specificity (Table 3).

The 47 TB cases and 23 subjects with LTBI were from ethnically diverse populations (comprising White Caucasians, South Asians and Black Africans); the results therefore indicate that Rv3615c can detect responses from *M. tb*-infected humans from genetically heterogeneous backgrounds, something which could not have been predicted from the results of Sidders et al in cattle.

This increase in sensitivity is clinically very important. A very high sensitivity allows doctors to rule out the possibility of tuberculosis when a diagnostic test is negative. In particular, immune based diagnostic tests (including the in vivo skin test) may give false negative results in immunosuppressed individuals because of their limited sensitivity. A higher diagnostic sensitivity will allow doctors to accurately detect tuberculosis infection even in these vulnerable immunosuppressed patients who are at the highest risk of severe and disseminated tuberculosis. 4% is considered a valuable and clinically important increment [Dosanjh et al Annals Internal Medicine 2008 148:325].

Unlike Sidders et al finding in cattle where the prevalence of interferon-gamma T cell responses to Rv3615c was only 37% (11 out of 30 experimentally infected cows), the prevalence of responses to our Rv3615c-derived 15-mer peptides in humans with tuberculosis (ie tuberculosis patients) was dramatically different at 72% (34/47 tuberculosis patients) (P<0.01, Chi-squared test), equivalent to the diagnostic sensitivity of ESAT-6 (72%) and CFP-10 (74%) demonstrated in this and other clinical studies of TB patients. This remarkable finding identifies Rv3615c as one of the 3 most immunodominant T cell antigens in *M. tb*-infected humans and could not have been predicted from Sidders at al's findings in cattle.

Table 3 shows how including Rv3615c peptides alongside ESAT-6 and CFP-10 peptides increases diagnostic sensitivity or active TB and LTBI without compromising specificity.

In conclusion, the use of Rv3615c for diagnosis or detection of active or latent tuberculosis infection is a potent new diagnostic tool for use in T cell-based assays. The Rv3615c diagnostic tool is at least as potent as ESAT-6 and CFP-10 and could therefore replace either ESAT-6 or CFP-10, which would be especially relevant if ESAT-6 were to be used as a vaccine. The promising ESAT-6-based vaccine comprising the ESAT-6-Ag85B fusion molecule could then be deployed once protective efficacy is confirmed in human clinical trials. This strategy would capitalise on the immunogenicity and preclinical protective efficacy of ESAT-6 to prevent tuberculosis through global vaccination without compromising the potent new T cell-based diagnostic paradigm which is improving tuberculosis control through targeted preventive treatment of latent tuberculosis infection.

Additionally, when used in combination with the ESAT-6 and CFP-10, IFN-gamma responses to Rv3615c provide incremental diagnostic sensitivity without reducing specificity in BCG-vaccinated populations.

Accordingly, in a first aspect, the invention provides a method of diagnosing *Mycobacterium tuberculosis* infection in a human, or of determining where a human has been exposed to *Mycobacterium tuberculosis*, comprising:
(i) contacting T-cells from said human with one or more of
(a) a peptide having the sequences listed as SEQ ID NO: 20
(b) a peptide having or comprising the sequence of at least 8 consecutive amino acids of the peptide listed as SEQ ID NO: 20; or
(c) a peptide having or comprising a sequence which is capable of binding to a T-cell receptor which recognises a peptide as defined in (a) or (b); and
determining whether any of the said T-cells recognise said peptide.

The method of the present invention provides a surprisingly high sensitivity in humans when used in the absence of any antigen which is not from Rv3615c. This high sensitivity in humans could not have been predicted based on the comparatively low sensitivity of 37% seen in cattle. In addition, the method of the present invention shows high sensitivity in latent TB infection (LTBI) as well as active TB.

| | | |
|---|---|---|
| Rv3615c/1 | MTENLTVQPERLGVL | SEQ ID NO 1 |
| Rv3616c/2 | TVQPERLGVLASHHD | SEQ ID NO 2 |
| Rv3615c/3 | RLGVLASHHDNAAVD | SEQ ID NO 3 |
| Rv3615c/4 | ASHHDNAAVDASSGV | SEQ ID NO 4 |
| Rv3615c/5 | NAAVDASSGVEAAAG | SEQ ID NO 5 |
| Rv3615c/6 | ASSGVEAAAGLGESV | SEQ ID NO 6 |
| Rv3615c/7 | EAAAGLGESVAITHG | SEQ ID NO 7 |
| Rv3615c/8 | LGESVAITHGPYCSQ | SEQ ID NO 8 |
| Rv3615c/9 | AITHGPYCSQFNDTL | SEQ ID NO 9 |
| Rv3615c/10 | PYCSQFNDTLNVYLT | SEQ ID NO 10 |
| Rv3615c/11 | FNDTLNVYLTAHNAL | SEQ ID NO 11 |
| Rv3615c/12 | NVYLTAHNALGSSLH | SEQ ID NO 12 |
| Rv3615c/13 | AHNALGSSLHTAGVD | SEQ ID NO 13 |
| Rv3615c/14 | GSSLHTAGVDLAKSL | SEQ ID NO 14 |
| Rv3615c/15 | TAGVDLAKSLRIAAK | SEQ ID NO 15 |
| Rv3615c/16 | LAKSLRIAAKIYSEA | SEQ ID NO 16 |
| Rv3615c/17 | RIAAKIYSEADEAWR | SEQ ID NO 17 |
| Rv3615c/18 | IYSEADEAWRKAIDG | SEQ ID NO 18 |
| Rv3615c/19 | DEAWRKAIDGLFT | SEQ ID NO 19 |

SEQ ID No. 20
MTENLTVQPERLGVLASHHDNAAVDASSGVEAAAGLGESVAITHGPYCSQ
FNDTLNVYLTAHNALGSSLHTAGVDLAKSLRIAAKIYSEADEAWRKAIDG
LFT

Multiple Rv3615c-derived peptides were widely recognised by T cells from an ethnically and genetically diverse range of patients and persons with LTBI, suggesting that these peptides may be recognised in the context of a wide range of HLA class II haplotypes, which is essential for effective vaccines which need to be highly recognised in infected individuals across the human population to be immunogenic and effective in genetically heterogeneous out-bred populations. Our findings with Rv3615c are reminiscent of the multiple promiscuous epitopes previously found in ESAT-6 and CFP-10.

T cell-derived IFN-gamma is essential in the activation of macrophages and containment of *M. tuberculosis* inside the granuloma. The critical role of IFN-gamma in the control of tuberculosis has been clearly demonstrated by the susceptibility to mycobacterial infections of mice with a disrupted IFN-gamma gene and of humans with defects in IFN-gamma response or production. As a consequence, the ability to stimulate T-cell release of IFN-gamma has been used as one of the most important criteria for the initial identification of vaccine antigens in antigen discovery programs. However, it is important to note that a strong vaccine-induced Th1 response (IFN-gamma release or frequency of IFN-gamma producing T cells) does not necessarily guarantee a high degree of protection. More recently, it has been recognised that the delineation of T cells into distinct functional populations defines the quality of the response, considered to be important for vaccine design. We know that ESAT-6 elicits a strong IFN-gamma and IFN-gamma/IL-2 polyfunctional responses in mice and humans it induces protection in mice. We have shown that Rv3615c also induces a strong IFN-gamma and polyfunctional IFN-gamma/IL-2 T cell response in LTBI, and is a target of both CD4 and CD8 T cells, the latter of which have also been identified to be important in protection against tuberculosis and are considered very important in tuberculosis vaccine development. Rv3615c is therefore a strong vaccine candidate.

Accordingly, in a second aspect of the present invention, there is provided an immunogenic composition comprising:
(i) (a) a non-cellular peptide having the sequences listed as SEQ ID NO: 20
(b) a non-cellular peptide having or comprising the sequence of at least 8 consecutive amino acids of the peptide listed as SEQ ID NO: 20; or
(c) a non-cellular peptide having or comprising a sequence which is capable of binding to a T-cell receptor which recognises a peptide as defined in (a) or (b); or
(ii) a non-cellular polynucleotide which is capable of expressing (i)

(iii) a recombinant organism engineered to express (i)
(iv) a recombinant organism engineered to upregulate expression or transport of (i).

There is also disclosed a method of prophylactic or therapeutic treatment of *Mycobacterium tuberculosis* infection or tuberculosis disease using the above composition.

A non-cellular peptide is a composition comprising the peptide and optionally other components including an adjuvant and an excipient. A non-cellular polynucleotide is a polynucleotide which is not contained within a cell, such as naked DNA, a recombinant virus, a plasmid or other types of vector.

Examples of recombinant organisms engineered to express the above peptide include bacteria and mycobacteria. Examples of recombinant organisms engineered to upregulate expression or transport of the above peptide include mycobacteria such as BCG.

DETAILED DESCRIPTION OF THE INVENTION

In a first aspect, the invention concerns diagnosis of tuberculosis infection in a human based on determination of whether the T cells of the human recognise an epitope of Rv3615c (SEQ ID No: 20). The method may also comprise determining whether T-cells of the human recognise one or more further *Mycobacterium tuberculosis* T-cell antigen(s), such as antigens encoded by the RD-1 or RD-2 region (preferably ESAT-6 and/or CFP10). In one embodiment the method comprises determining whether the T cell recognise one or more of the peptides represented by SEQ ID NOs 1 to 19. In another embodiment, the invention concerns a method of assessing or monitoring the immunogenicity or efficacy of a vaccine against *Mycobacterium tuberculosis* infection or tuberculosis disease by determining whether the CD4 and/or CD8 T-cells from a human recognise an epitope of Rv3615c (SEQ ID No: 20).

The human who is tested typically has an active or latent mycobacterial infection, or has had such an infection recently. The human may test positive or negative in a Mantoux test. The human may be at risk of a mycobacterial infection, typically for socio-economic reasons or may have a genetic or acquired predisposition to mycobacterial infection, e.g HIV infection.

The human may be a known or suspected contact who has been exposed to or may have been exposed to *Mycobacterium tuberculosis*. Typically the exposure is to pulmonary tuberculosis, such as "open" pulmonary tuberculosis which is sputum A.F.B. (acid-fast bacillus) smear positive. Thus the method may be used to trace the healthy contacts of individuals with such tuberculosis infections. The method may also be used to carry out population surveys to measure the number of individuals in a population who have a *Mycobacterium tuberculosis* infection. The contact may be someone whose exposure is a household, work place (such as a health care worker) or prison exposure (such as prisoner). The exposure may have resulted from residing in a country with high prevalence of TB, and diagnostic testing after emigration to a country with a low prevalence of TB. Thus the contact may be an immigrant.

The human who is tested (who has a known or suspected exposure) may be healthy or might have a chronic condition putting them at a higher risk of developing active TB and/or which may make TB infection harder to diagnose. Examples include HIV infected individuals, individuals taking immunosuppressants (e.g. corticosteroids, azathioprine and anti-TNF-α agents, such as infliximab, and cancer therapy), hemodialysis patients, organ transplant recipients, diabetics and very young children (aged under 5 years old, particularly under 2 years old).

The human who is tested may be a healthy participant in a phase 1, phase 2 or phase 3 clinical trial.

The T cells which recognise the peptide in the method are generally T cells which have been pre-sensitised in vivo to antigen from a *M. tuberculosis*. These antigen-experienced T cells are generally present in the peripheral blood of a host which has been exposed to the *M. tuberculosis* at a frequency of 1 in $10^6$ to 1 in $10^3$ peripheral blood mononuclear cells (PBMCs). The T cells may be CD4 and/or CD8 T cells.

In the method the T cells can be contacted with the peptides in vitro or in vivo, and determining whether the T cells recognise the peptide can be done in vitro or in vivo. Thus the invention provides a method of diagnosis which is practised on the human body.

Determination of whether the T cells recognise the peptide is generally done by detecting a change in the state of the T cells in the presence of the peptide or determining whether the T cells bind the peptide (e.g. using an MHC tetramer combined with FACS analysis system), i.e. the method of the invention does not necessarily rely on the detection of a functional response of the T cell.

In the case where a change in state of the T cells is detected, this is generally caused by antigen specific functional activity of the T cells after the T cell receptor binds the peptide. Generally when binding the T cell receptor, the peptide is bound to an MHC class I or II molecule, which is typically present on the surface of an antigen presenting cell (APC).

The change in state of the T cell may be the start of or increase in secretion of a substance from the T cell, such as a cytokine, especially IFN-γ, IL-2 or TNF-α. Simultaneous determination of IFN-γ and IL-2 secretion at the single cell level is particularly preferred and can enable monitoring of antigen and bacterial load, e.g. in response to treatment. Detection of IFN-γ secretion alone may suffice when only an initial diagnosis is required as in the examples below. Intracellular cytokine detection by FACS may be used. The substance can typically be detected by allowing it to bind to a specific binding agent and then measuring the presence of the specific binding agent/substance complex. Detection of the substance may be carried out using an ELISA based system. The specific binding agent is typically an antibody, such as polyclonal or monoclonal antibodies. Antibodies to cytokines are commercially available, or can be made using standard techniques.

Typically the specific binding agent is immobilised on a solid support. After the substance is allowed to bind, the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which is immobilised on a solid support. The bound IFN-γ is then detected using a second IFN-γ specific antibody which is labelled with a detectable label. Such a labelled antibody can be obtained from MABTECH (Stockholm, Sweden). Alternatively, fluorescence-based ELIPOST systems can be used to enable simultaneous detection of two or more cytokines (e.g. IFN-γ and IL-2) from individual T cells, which can then be enumerated as populations of single or dual cytokine-secreting T cells using fluorescent ELISpot readers which can be obtained from AID (Strassberg, Germany). Other detectable labels which can be used are discussed below.

The change in state of the T cell which can be measured may be the increase in the uptake of substances by the T cell, such as the uptake of thymidine. The change is state may be an increase in the size of the T cells, or proliferation of the T cells, or a change in cell surface markers on the T cell.

Generally the T cells which are contacted in the method are taken from the host in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 or only CD8 T cells, can be purified from the sample. PBMCs, MCs and T cells can be separated from the sample using techniques known in the art, such as those described in Lalvani et el (1997) *J. Exp. Med.* 186, p 859-865.

Preferably the T cells used in the assay are in the form of unprocessed or diluted samples, or are freshly isolated T cells (such as in the form of freshly isolated MCs or PBMCs) which are used directly ex viva, i.e. they are not cultured before being used in the method. However, the T cells can be cultured before use, for example in the presence of one or more of the peptides, and generally also exogenous growth promoting cytokines. During culturing the peptides are typically present on the surface of APCs, such as the APC used in the method. Pre-culturing of the T cells may lead to an increase in the sensitivity of the method. Thus the T cells can be converted into cell lines, such as short term cell lines (for example as described in Ota et al (1990) *Nature* 346, p 183-187).

The APC which is typically present in the method may from the same host as the T cell or from a different host. The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

Typically in the method, the T cells derived from the sample can be placed into an assay with all the peptides (i.e. a pool of the peptides) which it is intended to test (the relevant panel) or the T cells can be divided and placed into separate assays each of which contain one or more of the peptides. Preferably in the in vitro or in viva forms of the method.

The invention also provides the peptides such as two or more of any of the peptides mentioned herein (for example in any of the combinations mentioned herein) for simultaneous, separate or sequential use (eg. for in viva use).

In one embodiment peptide per se is added directly to an assay comprising T cells and APCs. As discussed above the T cells and APCs in such an assay could be in the form of MCs. When peptides which can be recognised by the T cell without the need for presentation by APCs are used then APCs are not required. Analogues which mimic the original peptide bound to a MHC molecule are an example of such a peptide.

In one embodiment the peptide is provided to the APC in the absence of the T cell. The APC is then provided to the T cell, typically after being allowed to present the peptide on its surface. The peptide may have been taken up inside the APC and presented, or simply be taken up onto the surface without entering inside the APC.

The duration for which the peptide is contacted with the T cells will vary depending on the method used for determining recognition of the peptide. Typically $10^5$ to $10^7$, preferably $5 \times 10^5$ to $10^6$ PBMCs are added to each assay. In the case where peptide is added directly to the assay its concentration is from $10^{-1}$ to $10^3$ µg/ml, preferably 0.5 to 50 µg/ml or 1 to 10 µg/ml.

15mer peptides overlapping adjacent peptides by 10 amino acid residues were used as opposed to Sidders et al who used 20mer peptides overlapping adjacent peptides by 12 amino acid residues. The advantage of 15mer peptides is that as well as efficiently detecting CD4 T cell responses, they also efficiently detect CD8 T cell responses—more efficiently than longer peptides, eg 18 or 20 a.a. long.

Typically the length of time for which the T cells are incubated with the peptide is from 4 to 24 hours (preferably 6 to 16 hours) for effector T cells or for more than 24 hours for central memory cells. When using ex vivo PBMCs it has been found that $0.3 \times 10^6$ PBMCs can be incubated in 10 µg/ml of peptide for 12 hours at 37° C.

The method may be based on an ELISA method, such as the whole blood Quantiferon system and its modifications (for example as available from Cellestis).

The determination of the recognition of the peptide by the cognate T cells may be done by detecting or measuring the binding to the T cells of the peptide presented in the context of HLA molecules with peptide-biding motifs congruent with the said peptide (e.g. peptide-HLA tetramers). Typically T cells which bind the peptide can be enumerated and sorted based on this binding, for example using fluorescently labelled monoclonal antibodies and a FACS machine. The presence of T cells which recognise the peptide will be deemed to occur if the frequency of cells sorted using the peptide is above a "control" value. The frequency of antigen-experienced T cells is generally 1 in $10^6$ to 1 in $10^3$ and therefore whether or not the sorted cells are antigen-experienced T cells can be determined.

The determination of the recognition of the peptide by the T cells may be measured in vivo. Typically the peptide is administered to the host and then a response which indicates recognition of the peptide may be measured. In the embodiment the peptide is administered intradermally, typically in a similar manner to the Mantoux test. The peptide may be administered epidermally. The peptide is typically administered by needle, such as by injection, but can be administered by other methods such as ballistics, for example the ballistics techniques which have been used to deliver nucleic acids. EP-A-0693119 describes techniques which can typically be used to administer the peptide. Typically from 0.001 to 1000 µg, for example from 0.01 to 100 µg or 0.1 to 10 µg of peptide is administered.

Alternatively an agent can be administered which is capable of providing the peptides in vivo. Thus a polynucleotide capable of expressing the peptide can be administered, typically in any of the way described above for the administration of the peptide. The polynucleotide typically has any of the characteristics of the polynucleotide provided by the invention which is discussed below. Peptide is expressed from the polynucleotide in vivo and recognition of the peptide in vivo is measured. Typically from 0.001 to 1000 μg, for example from 0.01 to 100 μg or 0.1 to 10 μg of polynucleotide is administered.

Recognition of the peptide in vivo is typically indicated by the occurrence of a DTH response. This is generally measured by visual examination of the site of administration of the peptide to determine the presence of inflammation, such as by the presence of induration, erythema or oedema.

The peptide capable of binding to a T-cell receptor which recognises a peptide having the sequence shown in SEQ ID NO: 20 or any other peptides to be tested (i.e. analogues of the peptide) may be identified by any suitable method. The binding of the peptide to the said T cell receptors can be tested by standard techniques. For example, T cell receptors can be isolated from T cells which have been shown to recognise the peptide having a sequence shown in SEQ ID NO: 20 (e.g. using the method of the invention). Demonstration of the binding of the peptide to the T cell receptors can then shown by determining whether the T cell receptors inhibit the binding of the peptide to a substance that binds the peptide, e.g. an antibody to the peptide. Typically the peptide is bound in an MHC molecule in such an inhibition of binding assay.

Typically the analogue inhibits the binding of the peptide to a T cell receptor. In this case the amount of peptide which can bind the T cell receptor in the presence of the analogue is decreased. This is because the analogue is able to bind the T cell receptor and therefore competes with a peptide for binding to the T cell receptor.

T cells for use in the above binding experiments can be isolated from patients with mycobacterial infection, for example with the aid of the method in the invention.

The analogue may have homology with the equivalent original peptide represented by one of SEQ ID NO: 20 or a sequence of at least 8 consecutive amino acids of SEQ ID NO: 20. A peptide which is homologous to another peptide is typically at least 70% homologous to the peptide, preferably at least 80 to 90% and more preferably at least 95%, 97% or 99% homologous thereto, for example over a region of at least 8, at least 15, preferably at least 30, for instance at least 40, 60 or 100 or more contiguous amino acids. Methods of measuring protein homology are well known in the art and it will be understood by those of skill in the art that in the present content, homology is calculated on the basis of amino acid identity (sometimes referred to as "hard homology"). For example the UWGCG Package provides the BESTFIT program which can be used to calculate homology (for example used on its default settings) (Devereux et al (1984) *Nucleic Acids Research* 12, p 387-395).

Typically the amino acids in the analogue at the equivalent positions to amino acids in the original peptide which contribute to binding the MHC molecule or are responsible for the recognition by the T cell receptor, are the same or are conserved.

Typically the analogue comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The peptide may comprise one or more non-natural amino acids, for example amino acids with a side chain different from natural amino acids. Generally, the non-natural amino acid will have an N terminus and/or a C terminus. The non-natural amino acid may be an L-amino acid.

The peptide typically has a shape, size, flexibility or electronic configuration which is substantially similar to the original peptide. It is typically a derivative of the original peptide.

In one embodiment the peptide is or mimics the original peptide bound to a MHC class II molecule. The analogue may be or may mimic the original peptide bound to 2, 3, 4 or more MHC class II molecules associated or bound to each other. These MHC molecules may be bound together using a biotin/streptavidin based system, in which typically 2, 3 or 4 biotin labelled MHC molecules bind to s streptavidin moiety. This peptide typically inhibits the binding of the peptide/MHC Class II complex to a T cell receptor or antibody which is specific for the complex. The analogue may be an antibody or a fragment of an antibody, such as a Fab or $(Fab)_2$ fragment.

The peptide may be immobilised on a solid support.

The peptide is typically designed by computational means and then synthesised using methods known in the art. Alternatively it can be selected from a library of compounds. The library may be a combinatorial library or a display library, such as a phage display library. The library of compounds may be expressed in the display library in the form of being bound to a MHC class II molecule, such as the MHC molecule which the original peptide binds. Peptides are generally selected from the library based on their ability to mimic the binding characteristics of the original peptides. Thus they may be selected based on ability to bind a T cell receptor or antibody which recognises the original peptide.

The invention also provides a kit for carrying out the method comprising one or more of the peptides and a means to detect the recognition of the peptide by the T cell. Typically the peptides are provided for simultaneous, separate or sequential use. Typically the means to detect recognition allows or aids detection based on the techniques discussed above.

Thus the means may allow detection of a substance secreted by the T cells after recognition. The kit may thus additionally include a specific binding agent for the substance, such as an antibody. The agent is typically specific for IFN-γ. The agent is typically immobilised on a solid support. This means that after binding the agent the substance will remain in the vicinity of the T cell which secreted it. Thus "spots" of substance/agent complex are formed on the support, each spot representing a T cell which is secreting the substance.

Quantifying the spots, and typically comparing against a control, allows determination of recognition of the peptide.

The kit may also comprise a means to detect the substance/agent complex. A detectable change may occur in the agent itself after binding the substance, such as a colour change. Alternatively a second agent directly or indirectly labelled for detection may be allowed to bind the substance/agent complex to allow the determination of the spots. As discussed above the second agent may be specific for the substance, but binds a different site on the substance than the first agent.

The immobilised support may be a plate with well, such as a microtitre plate. Each assay can therefore be carried out in a separate well in the plate.

The kit may additionally comprise medium for the T cells, detection agents or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the peptide, such as intradermal or epidermal administration. Typically such an instrument comprises one or more needles. The instrument may allow ballistic delivery of the peptide. The peptide in the kit may be in the form of a pharmaceutical composition.

The kit may also comprise controls, such as positive or negative controls. The positive control may allow the detection system to be tested. Thus the positive control typically mimics recognition of the peptide in any of the above methods. Typically in the kits designed to determine recognition in vitro the positive control is a cytokine. In the kit designed to detect in vivo recognition of the peptide the positive control may be antigen to which most individuals should response.

The kit may also comprise a means to take a sample containing T cells from the human, such as a blood sample. The kit may comprise a means to separate mononuclear cells or T cells from a sample from the human.

The invention also provides a composition comprising a peptide of the invention. The composition may be a pharmaceutical composition which further comprises a pharmaceutically acceptable carrier or diluent. Suitable carriers and diluents include isotonic saline solutions, for example phosphate-buffered saline. Typically the composition is formulated for intradermal or epidermal administration or for application by ballistic techniques. Thus the peptide or polynucleotide may be associated with a carrier particle for ballistic delivery.

The invention also related to a polynucleotide which is capable of expressing one or more peptides of the invention. Typically the polynucleotide is DNA or RNA, and is single or double stranded. The polynucleotide therefore typically comprises sequence which encodes the sequence of SEQ ID NO: 20 or a fragment thereof.

The polynucleotide may further comprise coding or noncoding sequences 5' and/or 3' to the sequence encoding the peptide. The sequences 5' and/or 3' to the coding sequence may comprise sequences which aid expression, such as transcription and/or translation, of the sequence encoding the peptide. The polynucleotide may be capable of expressing the peptide in a prokaryotic or eukaryotic cell. In one embodiment the polynucleotide is capable of expressing the peptide in a mammalian cell, such as a human, primate or rodent cell.

The polynucleotide may be incorporated into a replicable vector. Such a vector is able to replicate in a suitable cell. The vector may be an expression vector. In such a vector the polynucleotide of the invention is operable linked to a control sequence which is capable of providing for the expression or the polynucleotide. The vector may contain a selectable marker, such as the ampicillin resistance gene.

The polynucleotide of the invention, the peptides in a composition of the invention or the agents used in the method (for example in the detection of substances secreted from T cells) may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from Bio-Rad. Other suitable labels include other enzymes such as peroxidase, or protein labels, such as biotin; or radioisotopes, such as $^{32}P$ or $^{35}S$. The above labels may be detected using known techniques.

Polynucleotides of the invention or peptides in a composition of the invention may be in substantially purified form. They may be in substantially isolated form, in which case they will generally comprise at least 90%, for example at least 95, 97 or 99% of the polynucleotide, peptide or antibody in the preparation. The substantially isolated peptides generally comprise at least 90%, such as for example at least 95, 97 or 99% of the dry mass of the preparation.

The polynucleotide or peptide are typically substantially free of other cellular components or substantially free of other mycobacterial cellular components. The polynucleotide or peptide may be used in such a substantially isolated, purified or free form in the method or the present in such forms in the kit.

The peptide for use in the invention can be made using standard synthetic chemistry techniques, such as by use of an automated synthesizer.

The peptide is typically made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polypeptide typically has the sequence shown in SEQ ID NO: 20 and may have been expressed recombinantly.

The peptide can also be made in a process comprising expression of a polynucleotide, such as by expression of the polynucleotide of the invention. The expressed polypeptide may be further processed to produce the peptide of the invention. Thus the peptide may be made in a process comprising cultivating a cell transformed or transfected with an expression vector as described above under conditions to provide for expression of the peptide or a polypeptide from which the peptide can be made. The polynucleotide of the invention can be made using standard techniques, such as by using a synthesiser.

The invention also provides a method of ascertaining the stage of a *Mycobacterium tuberculosis* infection in a human comprising determining whether there is a differential T cell response to different *M. tb* antigens in the human. Any suitable method mentioned herein may be used to measure the T cell responses. The T cell responses may be to any of the *M. tb* peptides mentioned herein, such as one or more of Rv3615c, ESAT-6 or CFP10. The method may be carried out to determine whether the infection is recent or longstanding, to determine whether the human is latently infected or has disease, or to monitor the effect of treatment.

EXAMPLES

Forty-seven adult patients with active TB disease (culture-confirmed, n=25; clinically highly probable, n=22) were assessed for the presence of T cell responses to pools of overlapping 15mer peptides (each peptide overlapping its neighbour by 10 amino acids) spanning the length of the *M. tuberculosis* antigens Rv3615c, ESAT-6 and CFP-10 in venous blood samples drawn after informed written consent. Diagnostic classification of the patients was based on categories 1 and 2 in Table 1 below (see Dosanjh et al *Ann Intern Med* 2008; 148: 325-336) and T cell responses were enumerated using ex vivo IFN-gamma ELISpot assay, as previously described (Dosanjh et al *Ann Intern Med* 2008; 148: 325-336). 29 of the 47 TB cases had had no treatment at the point of assessment and the remainder had had less than 2 months treatment (full course of treatment=6 months).

In addition, 23 healthy persons with presumed latent TB infection (LTBI) were assessed for T cell responses to the peptides from Rv3615c, ESAT-6 and CFP-10 as above. Diagnostic classification of these subjects was based on category 4B in Table 1 below. All these individuals had a clear history of TB exposure, were asymptomatic, had positive tuberculin skin tests (>10 mm cutaneous induration on Mantoux testing) and normal chest radiography. None of the 23 LTBI subjects had started preventive treatment at the point of assessment.

Finally, 31 healthy asymptomatic BCG-vaccinated volunteers with no known history of TB exposure or disease were assessed as above, serving as negative controls for the presence of TB infection.

TABLE 1

Diagnostic classification of subjects in the present examples. The 47 patients with active TB were from diagnostic categories 1 (culture-confirmed) and 2 (clinically highly probable), the 23 subjects with LTBI were from category 4B and the BCG-vaccinated healthy negative controls were from category 4D.

| Diagnostic Category | Criteria |
| --- | --- |
| 1: Culture-confirmed tuberculosis | Microbiological culture of *Mycobacterium tuberculosis* and Suggestive clinical and radiologic findings |
| 2: Highly probable tuberculosis | Clinical and radiologic features highly suggestive of tuberculosis and unlikely to be caused by other disease and A decision to treat made by a clinician and Appropriate response to therapy and Histology supportive if available† |
| 3: Clinically indeterminate | A final diagnosis of tuberculosis was neither highly probable nor reliably excluded |
| 4: Active tuberculosis excluded | All microbiological samples smear and culture negative and A definite alternative diagnosis identified |
| Subclassification | |
| 4A: Inactive tuberculosis | Previous episode or stable chest radiograph changes and TST positive‡ (if done) and Bacteriologically negative (if done) and No clinical evidence of active disease |
| 4B: ≥1 risk factors for tuberculosis exposure§. TST positive | TST positive and Bacteriologically negative (if done) and No clinical evidence of active disease |
| 4C: ≥1 risk factors for tuberculosis exposure§. TST negative | History of tuberculosis exposure and TST negative (if done) |
| 4D: No risk factors for tuberculosis exposure§. TST negative | No history of tuberculosis exposure and TST negative (if done) |

TABLE 2

Rates of positive T cell responses to peptide pools from ESAT-6, CFP-10 and Rv3615c measured by ex vivo IFN-gamma ELISpot in 47 TB patients, 23 people with latent TB infection and 31 healthy controls with no history of TB exposure or contact.

| | Cases | | | | Controls | |
| --- | --- | --- | --- | --- | --- | --- |
| | n | % | LTBI | | n | % |
| ESAT-6 | 34/47 | 72 | 12/23 | 52 | 2/31 | 6 |
| CFP-10 | 35/47 | 74 | 15/23 | 65 | 2/31 | 6 |
| Rv3615c | 34/47 | 72 | 14/23 | 61 | 2/31 | 6 |

The prevalence of T cell responses to Rv3615c peptides in active TB cases is as high as for T cell responses to ESAT-6 and CFP-10, indicating that the diagnostic sensitivity of Rv3615c is as high as ESAT-6 and CFP10. The diagnostic sensitivity of Rv3615c in active TB cases (34/47, 72%) is statistically significantly higher than its sensitivity in cattle with active TB as described by Sidders et al (11/30, 37%), P<0.01. This is the first demonstration of a diagnostic sensitivity for Rv3615c in active TB in mammals, as Sidders et al only studied cattle with positive skin tests, ie the cattle did not have pathological or microbiological diagnosis of active TB.

The prevalence of T cell responses to Rv3615c in subjects with LTBI is approximately as high as that for ESAT-6 and CFP-10, indicating that the diagnostic sensitivity of Rv3615c in LTBI is as high as ESAT-6 and CFP-10.

The prevalence of responses to Rv3615c in unexposed controls is as low as that for ESAT-6 and CFP-10, indicating that the diagnostic specificity of Rv3615c is as high as ESAT-6 and CFP-10.

The 47 TB cases and 23 subjects with LTBI were from ethnically diverse populations (comprising White Caucasians, South Asians and Black Africans); the results therefore indicate that Rv3615c can detect responses from *M. tb*-infected humans from genetically heterogeneous backgrounds, something which could not have been predicted from the results of Sidders et al in cattle.

TABLE 3

Rates of positive T cell responses to combinations of the peptide pools from ESAT-6, CFP-10 and Rv3615c measured by IFN-gamma ELISpot in 47 TB patients, 23 people with latent TB infection and 31 healthy controls with no history of TB exposure or contact.

| | Cases | | LTBI | | Controls | |
| --- | --- | --- | --- | --- | --- | --- |
| | n | % | n | % | N | % |
| ESAT-6/CFP-10 | 42/47 | 89 | 16/23 | 70 | 2/31 | 6 |
| ESAT-6/CFP-10/Rv3615c | 44/47 | 94 | 18/23 | 78 | 2/31 | 6 |
| ESAT-6/Rv3615c | 41/47 | 87 | 16/23 | 70 | 2/31 | 6 |
| CFP-10/Rv3615c | 44/47 | 94 | 16/23 | 70 | 2/31 | 6 |

Rv3615c can serve as a replacement for ESAT-6 or CFP-10; when used in conjunction with either of these antigens, it provides diagnostic sensitivity at least as high as the conventional ESAT-6/CFP-10 combination.

When added to the combination of ESAT-6/CFP-10, Rv3615c increases diagnostic sensitivity in active TB (by 5% in this series of 47 patients) and LTBI (by 8%) without reducing diagnostic specificity, although the samples size here is too small to meaningfully test for statistical significance.

TABLE 4

Proportion of active TB cases and LTBI subjects that responded to the pool of Rv3615c peptides who respond to each of the individual peptides, using ex vivo IFN-gamma ELISpot assay. Denominators are the numbers responders to the peptide pool that were tested against each of the individual constituent peptides of the pool. Numerators are the number of subjects responding to the individual constituent 15mer peptides.

| | Cases | | LTBI | |
| --- | --- | --- | --- | --- |
| Rv3615c | n | % | n | % |
| p1 | 1/15 | 7 | 0/5 | 0 |
| p2 | 5/15 | 33 | 0/5 | 0 |
| p3 | 3/15 | 20 | 2/5 | 40 |
| p4 | 2/15 | 13 | 1/5 | 20 |

TABLE 4-continued

Proportion of active TB cases and LTBI subjects that responded to the pool of Rv3615c peptides who respond to each of the individual peptides, using ex vivo IFN-gamma ELISpot assay. Denominators are the numbers responders to the peptide pool that were tested against each of the individual constituent peptides of the pool. Numerators are the number of subjects responding to the individual constituent 15mer peptides.

| Rv3615c | Cases | | LTBI | |
|---|---|---|---|---|
| | n | % | n | % |
| p5 | 2/15 | 13 | 1/5 | 20 |
| p6 | 1/15 | 7 | 0/5 | 0 |
| p7 | 1/15 | 7 | 0/5 | 0 |
| p8 | 1/15 | 7 | 0/5 | 0 |
| p9 | 0/15 | 0 | 2/5 | 40 |
| p10 | 6/15 | 40 | 2/5 | 40 |
| p11 | 4/15 | 27 | 0/5 | 0 |
| p12 | 6/14 | 43 | 2/5 | 40 |
| p13 | 3/14 | 21 | 0/4 | 0 |
| p14 | 11/14 | 79 | 2/4 | 50 |
| p15 | 10/14 | 71 | 2/4 | 50 |
| p16 | 9/13 | 69 | 4/4 | 100 |
| p17 | 5/13 | 38 | 2/2 | 50 |
| p18 | 1/13 | 8 | 1/4 | 25 |
| p19 | 2/13 | 15 | 1/4 | 25 |

BRIEF DESCRIPTION OF DRAWINGS

FIG. 1 is a graphic representation of the data from Table 4.

This is the first mapping of the location of T cell epitopes in Rv3615c in *M. tb*-infected humans, and is here defined for both active TB cases and subjects with LTBI.

The mapping indicates 2 regions that contain widely-recognised T cell epitopes of diagnostic utility: a region towards the carboxy terminal (peptides 9-19; amino acid residues 46-95) and a second region towards the amino terminal (peptides 2-5; amino acid residues 6-36)

The first region of concentration of widely recognised T cell epitopes was not observed in cattle by Sidders et al.

This epitope map is reliable and relevant to humans because (a) it is carried out in humans, (b) it based on approximately 20 subjects (hence considerably more reliable and definitive than the data from Sidders et al which was based on just 3 cows and (c) it is from an out-bred genetically heterogeneous human populations including persons of various distinct ethnicities (including White Caucasians, South Asians, Black Africans).

It illustrates the locations of epitopes in active TB for the first time in any mammal (Sidders et al studied only cattle with positive skin tests)

Figure 1:
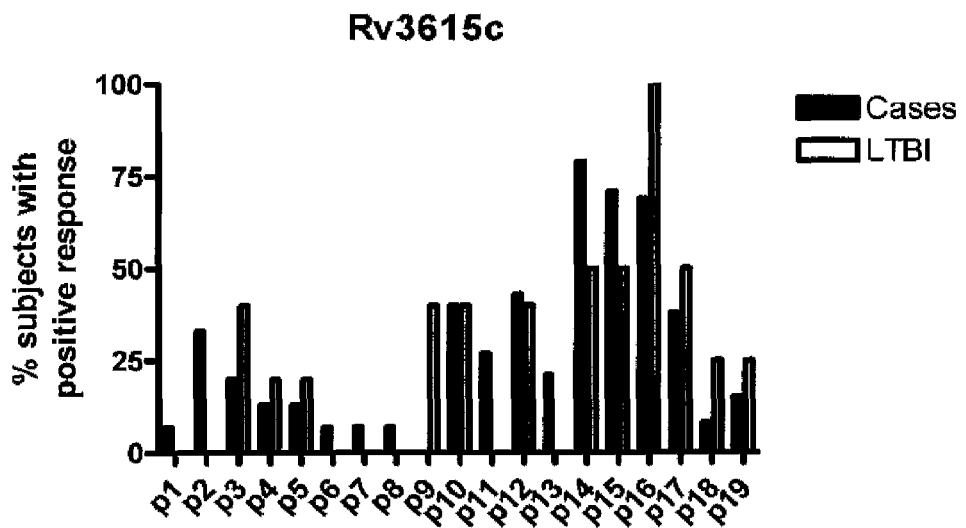
FIG. 1 shows the proportion of active TB cases and LTBI subjects that responded to the pool of Rv3615c peptides who respond to each of the individual peptides.
Figure 2A:
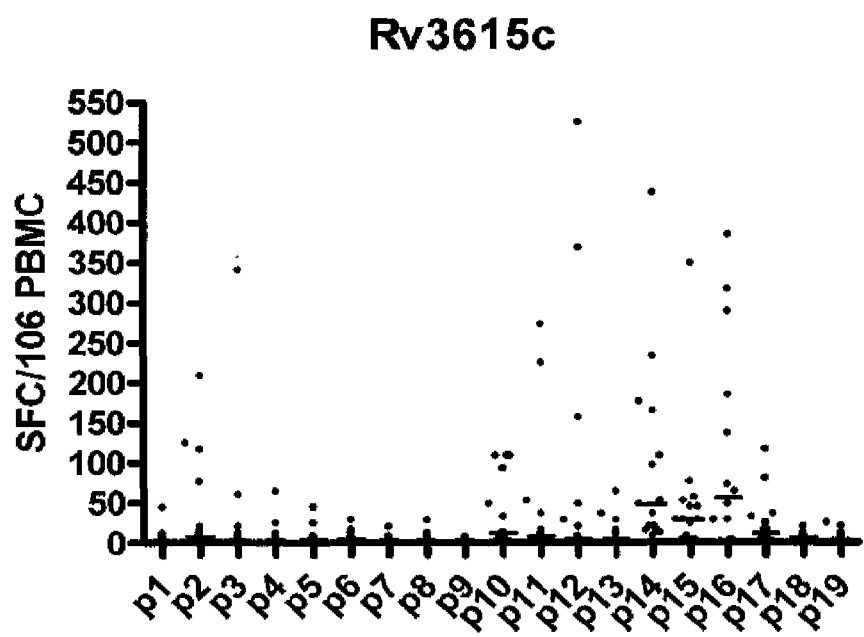
Figure 2B:
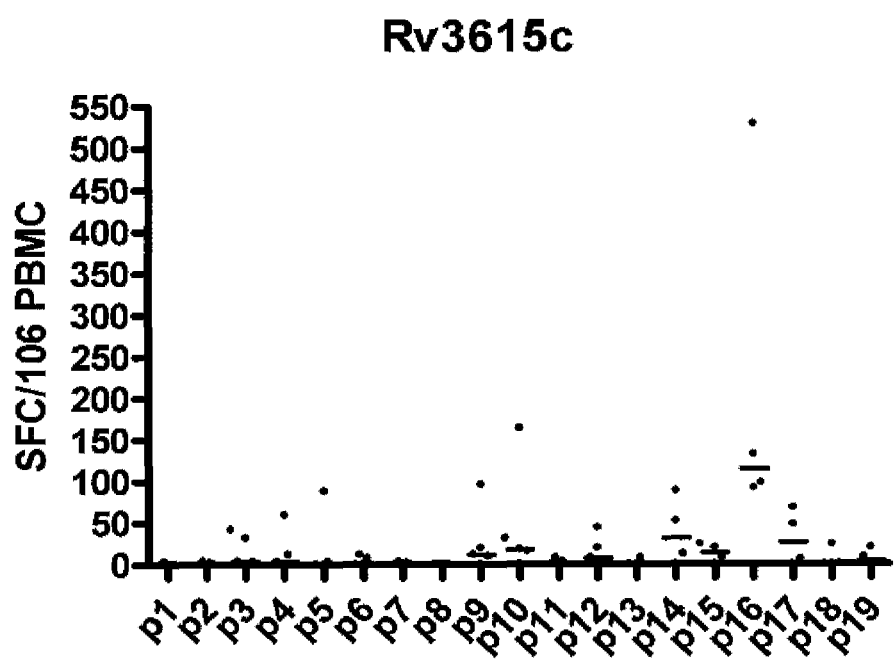

It uses 15mer peptides overlapping by 10 amino acids and is therefore distinct from, and has a higher resolution than, maps that use longer peptides FIG. 2A shows the frequency of IFN-gamma spot forming cells (SFCs) responding to each of the constituent 15mer peptides of Rv3615c in 15 active TB cases. FIG. 2B shows the frequency of IFN-gamma spot forming cells (SFCs) responding to each of the constituent 15mer peptides of Rv3615c in 5 LTBI subjects.

Figure 3:
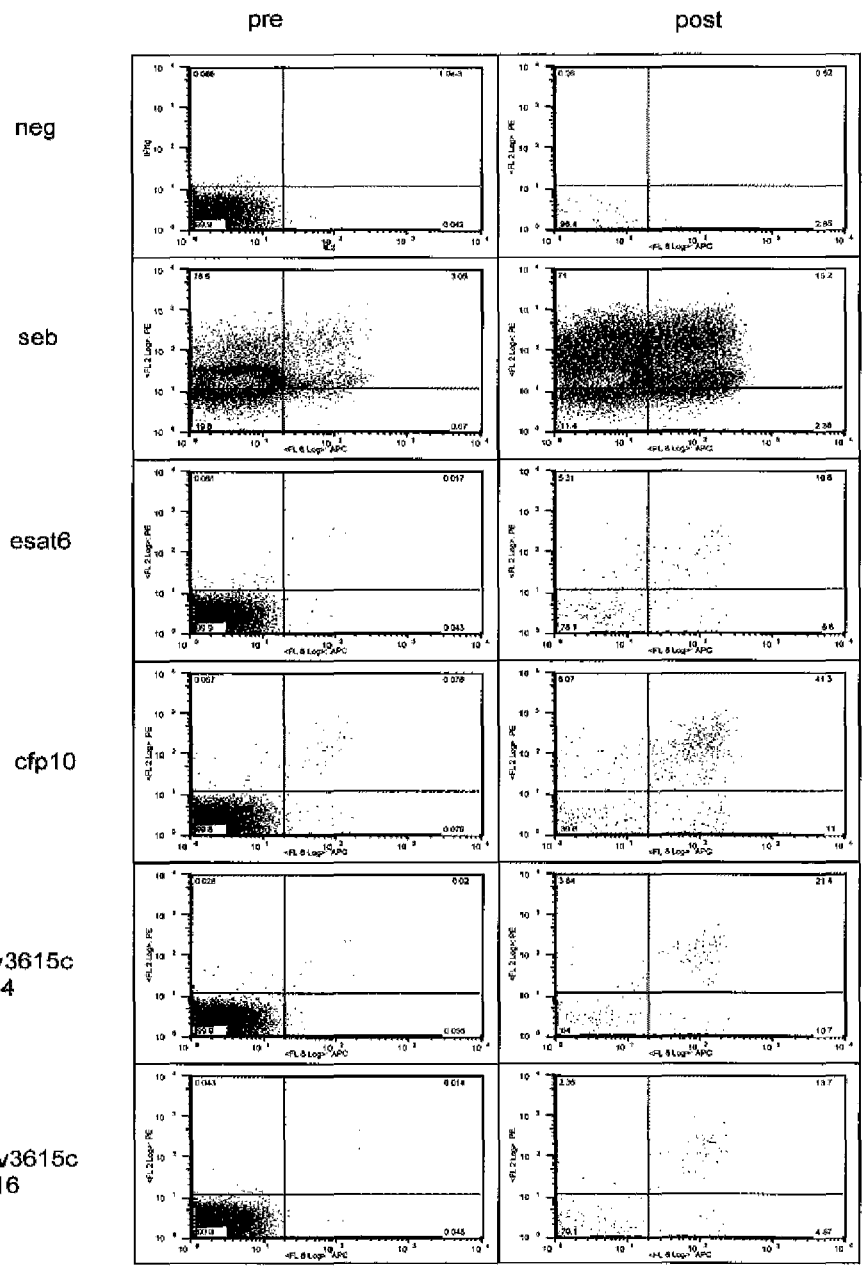

FIG. 3 shows a FACS analysis following cytokine capture assay (Miltenyi Biotech, Germany) of CD4-positive T cells secreting IFN-gamma, IL-2 or both in response to 6 hour stimulation with Rv3615c peptides (and, as controls, ESAT-6 peptide pool, CFP-10 peptide pool, Staphylococcal enterotoxin B [SEB, positive control], no stimulus [neg, negative control]). CD4 T cells responding to Rv3615c peptides (p14 and p16 in this example) from subject T416 (LTBI) belong to 3 distinct subsets: T cells secreting both IFN-gamma and IL-2 (dominant population), T cells secreting IL-2 only (second largest population) and T cells secreting IFN-gamma only (smallest population).

Figure 4:
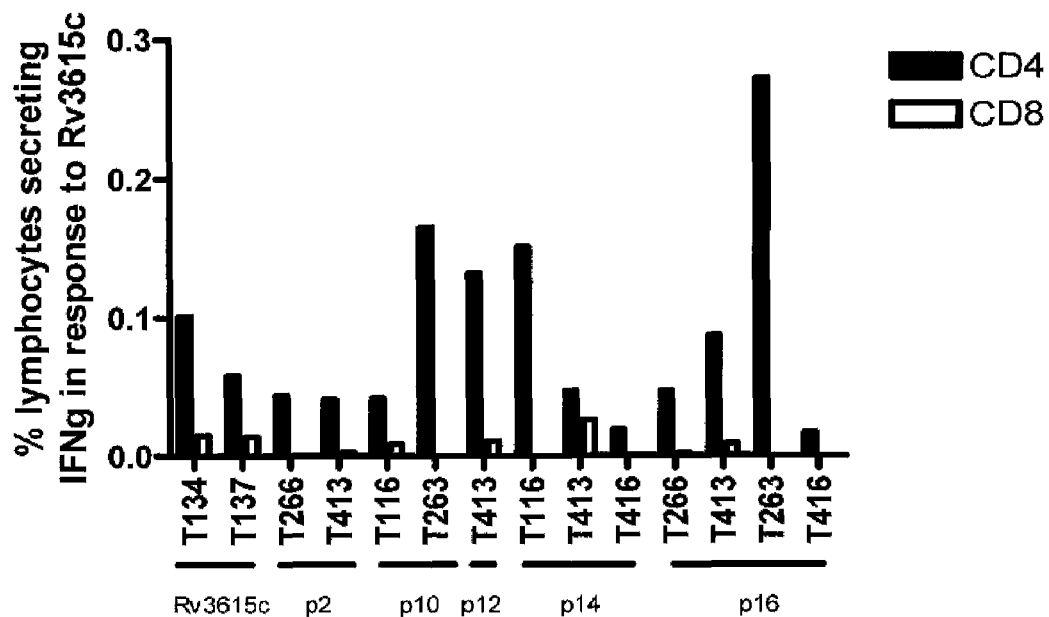

FIG. 4 shows the proportions of CD4 and CD8 T cells secreting IFN-gamma in response to Rv3615c peptides p2, p10, p12, p14 and p16. TB Cases are T134; T137; T116; T266; T413. LTBI cases are T263; 1416.

Figure 5:
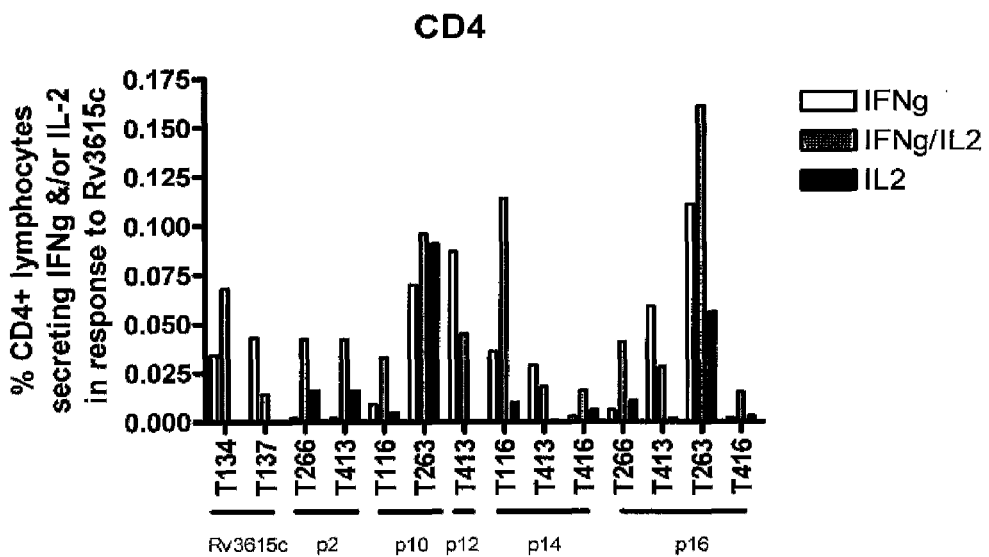

FIG. 5 shows the proportion of CD4 T cells secreting IFN-gamma only, IL-2 only and both IFN-gamma and IL-2 in response to Rv3615c peptides p2, p10, p12, p14 and p16. TB Cases are T134; T137; T116; T266; T413. LTBI cases are T263; T416.

Figure 6:
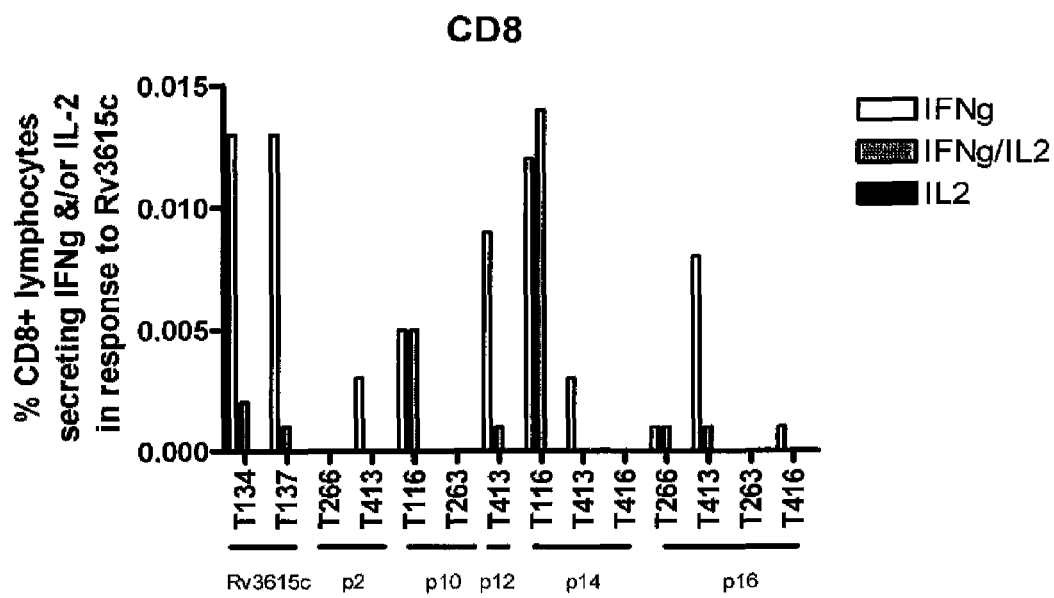

FIG. 6 show the proportion of CD8 T cells secreting IFN-gamma only, IL-2 only and both IFN-gamma and IL-2 in response to Rv3615c peptides p2, p10, p12, p14 and p16. TB Cases are 1134; 1137; 1116; T266; 1413. LTBI cases are T263; T416.

Figure 7:
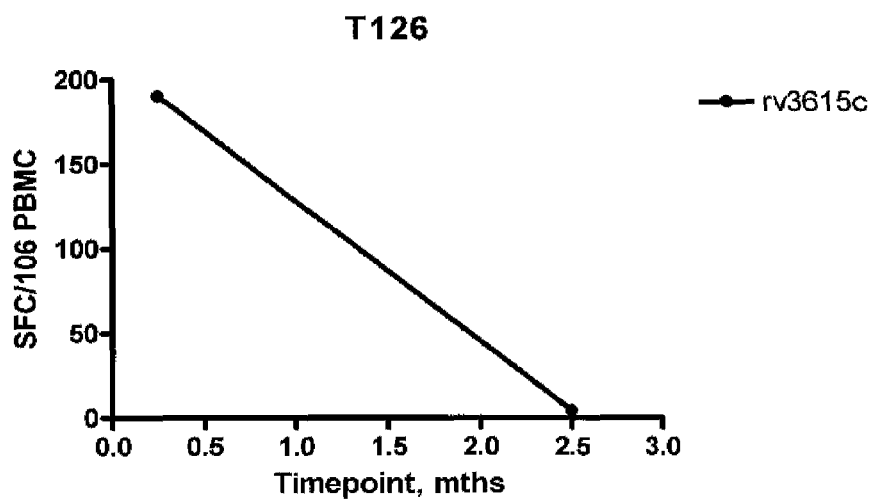

FIG. 7 shows the decline in IFN-gamma ex vivo ELISpot response to Rv3615c peptide pool in after initiation of anti-TB treatment, in parallel with decline in antigen load and bacterial burden. In FIG. 7, N=1 for T126 there is no rv2654 data at 0.25 and 2.5 months.

The invention claimed is:

1. A method of diagnosing *Mycobacterium tuberculosis* infection in a human, or of determining whether a human has been exposed to *Mycobacterium tuberculosis*, comprising:
   (i) contacting T-cells from a sample from said human, wherein said sample comprises T-cells and optionally monocytes, with one or more of
      (a) a peptide consisting of the sequence shown in SEQ ID NO 20
      (b) a peptide consisting of the sequence of at least 8 consecutive amino acids of the sequence shown in SEQ ID NO 20; or
      (c) a peptide consisting of a sequence which is capable of binding to a T-cell receptor which recognizes a peptide consisting of the sequence shown in SEQ ID NO. 20 or a sequence of at least 8 consecutive amino acids of the sequence shown in SEQ ID 20; and
   (ii) determining whether any of the said T-cells recognize said peptide, wherein recognition of said peptide by said T-cells is determined by detecting the secretion of a cytokine from the T-cells or a chemokine from monocytes, where present, in a sample containing the T-cells and wherein steps (i) and (ii) are optionally carried out in vitro.

2. The method of claim 1, wherein the method increases the sensitivity of a diagnostic test for diagnosing *Mycobacterium tuberculosis* infection in a human, wherein said diagnostic test additionally comprises contacting T cells from said human with *Mycobacterium tuberculosis* antigen which is not Rv3615c.

3. A method according to claim 1 or 2, wherein step (i) further comprises contacting said T-cells with one or more further *Mycobacterium tuberculosis* T-cell antigen(s) or with an analogue(s) of said antigen(s) which is capable of binding to a T-cell receptor which recognizes said antigen(s).

4. A method according to claim 3, wherein said one or more further T-cell antigens include antigens encoded by the RD-1 or RD-2 region, which antigens are preferably ESAT-6 and/or CFP10; or fragments thereof which are at least 8 amino acids long.

5. A method according to claim 1, wherein the T-cells are not contacted with any *Mycobacterium tuberculosis* antigen which is not from Rv3615c.

6. A method according to claim 1, wherein step (i) comprises contacting said sample of T-cells with two or more different peptides, each having the sequence of at least 8 consecutive amino acids of the sequence shown in SEQ ID NO 20.

7. A method according to claim 1 wherein peptides further including peptides from, or analogues of, at least five different antigens are contacted with the T cells.

8. A method according to claim 1 wherein one or more of the peptides:
   (i) is represented by SEQ ID NOs 1 to 19, or
   (ii) binds to a T-cell which recognizes (i),
   are contacted with the T-cells.

9. A method according to claim 1, wherein said cytokine is IFN-γ and/or IL-2 and/or TNF-α and/or the chemokine is IP10.

10. A method according to claim 1, wherein said cytokine is detected by allowing said cytokine to bind to an immobilised antibody specific to said cytokine and detecting the presence of the antibody/cytokine complex.

11. A method according to claim 1, wherein said T-cells are freshly isolated ex vivo cells.

12. A method according to claim 1, wherein said T-cells have been cultured in vitro.

13. A method according to claim 1, wherein the *Mycobacterium tuberculosis* infection is latent TB infection (LTBI).

14. A kit for diagnosing *Mycobacterium tuberculosis* infection or exposure in a human, said kit comprising a composition comprising,
   (a) a peptide consisting of the sequence shown in SEQ ID NO 20;
   (b) a peptide consisting of the sequence of at least 8 consecutive amino acids of the sequence shown in SEQ ID NO 20; or
   (c) a peptide consisting of a sequence which is capable of binding to a T-cell receptor which recognizes a peptide as defined in (a) or (b); or
   (d) at least one peptide:
      (i) which is represented by SEQ ID NOs 1 to 19, or
      (ii) which binds to a T-cell which recognizes (i),
   and the composition optionally comprises one or more further *Mycobacterium tuberculosis* T-cell antigens,
   wherein the kit comprises a means for detecting recognition of a peptide by T-cells, wherein said means for detecting recognition of a peptide by T-cells comprises an antibody to a cytokine and wherein said antibody is immobilised on a solid support and wherein said kit optionally comprises a means to detect an antibody/cytokine complex.

15. A method according to claim 1, wherein determination of a differential T cell response is carried out:

(i) to determine whether the infection is recent or long-standing, or
   (ii) to determine whether the human is latently infected or has disease, or
   (iii) to monitor the effect of treatment.

16. A method of prophylactic or therapeutic treatment of *Mycobacterium tuberculosis* infection or tuberculosis disease, the method comprising:
   administering to a subject an immunogenic composition in an amount effective to produce an immunogenic response, wherein the immunogenic composition comprises:
   (i) a non-cellular peptide wherein the peptide is:
      (a) a peptide consisting of the sequence shown in SEQ ID NO 20
      (b) a peptide consisting of the sequence of at least 8 consecutive amino acids of the sequence shown in SEQ ID NO 20; or
      (c) a peptide consisting of a sequence which is capable of binding to a T-cell receptor which recognizes a peptide as defined in (a) or (b); or
      (d) at least one peptide: (I) which is represented by SEQ ID NOs 1 to 19, or (II) which binds to a T-cell which recognizes (I); or
   (ii) a non-cellular polynucleotide which is capable of expressing (i)
   (iii) a recombinant organism engineered to express the peptide wherein the peptide is:
      (a) a peptide consisting of the sequence shown in SEQ ID NO 20
      (b) a peptide consisting of the sequence of at least 8 consecutive amino acids of the sequence shown in SEQ ID NO 20; or
      (c) a peptide consisting of a sequence which is capable of binding to a T-cell receptor which recognizes a peptide as defined in (a) or (b); or
      (d) at least one peptide: (I) which is represented by SEQ ID NOs 1 to 19, or (II) which binds to a T-cell which recognize (I);
   (iv) a recombinant organism engineered to upregulate expression or transport of the peptide wherein the peptide is:
      (a) a peptide consisting of the sequence shown in SEQ ID NO 20
      (b) a peptide consisting of the sequence of at least 8 consecutive amino acids of the sequence shown in SEQ ID NO 20; or
      (c) a peptide consisting of a sequence which is capable of binding to a T-cell receptor which recognizes a peptide as defined in (a) or (b); or
      (d) at least one peptide: (I) which is represented by SEQ ID NOs 1 to 19, or (II) which binds to a T-cell which recognizes (I),
   wherein recognition of said peptide by said T-cells is determined by detecting the secretion of a cytokine from the T-cells or a chemokine from monocytes in a sample containing the T-cells.

17. The method of claim 16, wherein the subject is a mammal.

18. The method of claim 17, wherein the mammal is a human.

19. A method according to claim 16, wherein the composition is administered to prime or to boost immune response.

20. The method of claim 16, additionally comprising a step of assessing or monitoring the immunogenicity or efficacy of the immunogenic composition against *Mycobacterium tuberculosis* infection or tuberculosis disease comprising (i) contacting T-cells from a sample from the subject, wherein said sample comprises T-cells and optionally monocytes with one or more of:
(a) a peptide consisting of the sequence shown in SEQ ID NO 20
(b) a peptide consisting of the sequence of at least 8 consecutive amino acids of the sequence shown in SEQ ID NO 20; or
(c) a peptide consisting of a sequence which is capable of binding to a T-cell receptor which recognizes a peptide as defined in (a) or (b); and
(ii) determining whether any of the said T-cells recognize said peptide, wherein steps (i) and (ii) are optionally carried out in vitro, wherein recognition of said peptide by said T-cells is determined by detecting the secretion of a cytokine from the T-cells or a chemokine from monocytes, where present, in a sample containing the T-cells.

21. A method of ascertaining the stage of *Mycobacterium tuberculosis* infection in a human comprising:

(i) contacting T-cells from a sample from said human, wherein said sample comprises T-cells and optionally monocytes with one or more of
(a) a peptide consisting of the sequence shown in SEQ ID NO 20
(b) a peptide consisting of the sequence of at least 8 consecutive amino acids of the sequence shown in SEQ ID NO 20; or
(c) a peptide consisting of a sequence which is capable of binding to a T-cell receptor which recognizes a peptide as defined in (a) or (b); and
(iii) determining whether any of the said T-cells recognize said peptide, wherein steps (i) and (ii) are optionally carried out in vitro; and
determining whether there is a differential T cell response to one or more other antigens, wherein recognition of said peptide by said T-cells is determined by detecting the secretion of a cytokine from the T-cells or a chemokine from monocytes, where present, in a sample containing the T-cells.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Mycobacterium tuberculosis

<400> SEQUENCE: 1

Met Thr Glu Asn Leu Thr Val Gln Pro Glu Arg Leu Gly Val Leu
1               5                   10                  15

<210> SEQ ID NO 2
<211> LENGTH: 15
<212> TYPE: PRT
<213> ORGANISM: Mycobacterium tuberculosis

<400> SEQUENCE: 2
```

-continued

```
Thr Val Gln Pro Glu Arg Leu Gly Val Leu Ala Ser His His Asp
1               5                   10                  15

<210> SEQ ID NO 3
<211> LENGTH: 15
<212> TYPE: PRT
<213> ORGANISM: Mycobacterium tuberculosis

<400> SEQUENCE: 3

Arg Leu Gly Val Leu Ala Ser His His Asp Asn Ala Ala Val Asp
1               5                   10                  15

<210> SEQ ID NO 4
<211> LENGTH: 15
<212> TYPE: PRT
<213> ORGANISM: Mycobacterium tuberculosis

<400> SEQUENCE: 4

Ala Ser His His Asp Asn Ala Ala Val Asp Ala Ser Ser Gly Val
1               5                   10                  15

<210> SEQ ID NO 5
<211> LENGTH: 15
<212> TYPE: PRT
<213> ORGANISM: Mycobacterium tuberculosis

<400> SEQUENCE: 5

Asn Ala Ala Val Asp Ala Ser Ser Gly Val Glu Ala Ala Ala Gly
1               5                   10                  15

<210> SEQ ID NO 6
<211> LENGTH: 15
<212> TYPE: PRT
<213> ORGANISM: Mycobacterium tuberculosis

<400> SEQUENCE: 6

Ala Ser Ser Gly Val Glu Ala Ala Ala Gly Leu Gly Glu Ser Val
1               5                   10                  15

<210> SEQ ID NO 7
<211> LENGTH: 15
<212> TYPE: PRT
<213> ORGANISM: Mycobacterium tuberculosis

<400> SEQUENCE: 7

Glu Ala Ala Ala Gly Leu Gly Glu Ser Val Ala Ile Thr His Gly
1               5                   10                  15

<210> SEQ ID NO 8
<211> LENGTH: 15
<212> TYPE: PRT
<213> ORGANISM: Mycobacterium tuberculosis

<400> SEQUENCE: 8

Leu Gly Glu Ser Val Ala Ile Thr His Gly Pro Tyr Cys Ser Gln
1               5                   10                  15

<210> SEQ ID NO 9
<211> LENGTH: 15
<212> TYPE: PRT
<213> ORGANISM: Mycobacterium tuberculosis

<400> SEQUENCE: 9

Ala Ile Thr His Gly Pro Tyr Cys Ser Gln Phe Asn Asp Thr Leu
```

```
<210> SEQ ID NO 10
<211> LENGTH: 15
<212> TYPE: PRT
<213> ORGANISM: Mycobacterium tuberculosis

<400> SEQUENCE: 10

Pro Tyr Cys Ser Gln Phe Asn Asp Thr Leu Asn Val Tyr Leu Thr
1               5                   10                  15

<210> SEQ ID NO 11
<211> LENGTH: 15
<212> TYPE: PRT
<213> ORGANISM: Mycobacterium tuberculosis

<400> SEQUENCE: 11

Phe Asn Asp Thr Leu Asn Val Tyr Leu Thr Ala His Asn Ala Leu
1               5                   10                  15

<210> SEQ ID NO 12
<211> LENGTH: 15
<212> TYPE: PRT
<213> ORGANISM: Mycobacterium tuberculosis

<400> SEQUENCE: 12

Asn Val Tyr Leu Thr Ala His Asn Ala Leu Gly Ser Ser Leu His
1               5                   10                  15

<210> SEQ ID NO 13
<211> LENGTH: 15
<212> TYPE: PRT
<213> ORGANISM: Mycobacterium tuberculosis

<400> SEQUENCE: 13

Ala His Asn Ala Leu Gly Ser Ser Leu His Thr Ala Gly Val Asp
1               5                   10                  15

<210> SEQ ID NO 14
<211> LENGTH: 15
<212> TYPE: PRT
<213> ORGANISM: Mycobacterium tuberculosis

<400> SEQUENCE: 14

Gly Ser Ser Leu His Thr Ala Gly Val Asp Leu Ala Lys Ser Leu
1               5                   10                  15

<210> SEQ ID NO 15
<211> LENGTH: 15
<212> TYPE: PRT
<213> ORGANISM: Mycobacterium tuberculosis

<400> SEQUENCE: 15

Thr Ala Gly Val Asp Leu Ala Lys Ser Leu Arg Ile Ala Ala Lys
1               5                   10                  15

<210> SEQ ID NO 16
<211> LENGTH: 15
<212> TYPE: PRT
<213> ORGANISM: Mycobacterium tuberculosis

<400> SEQUENCE: 16

Leu Ala Lys Ser Leu Arg Ile Ala Ala Lys Ile Tyr Ser Glu Ala
1               5                   10                  15
```

```
<210> SEQ ID NO 17
<211> LENGTH: 15
<212> TYPE: PRT
<213> ORGANISM: Mycobacterium tuberculosis

<400> SEQUENCE: 17

Arg Ile Ala Ala Lys Ile Tyr Ser Glu Ala Asp Glu Ala Trp Arg
1               5                   10                  15

<210> SEQ ID NO 18
<211> LENGTH: 15
<212> TYPE: PRT
<213> ORGANISM: Mycobacterium tuberculosis

<400> SEQUENCE: 18

Ile Tyr Ser Glu Ala Asp Glu Ala Trp Arg Lys Ala Ile Asp Gly
1               5                   10                  15

<210> SEQ ID NO 19
<211> LENGTH: 13
<212> TYPE: PRT
<213> ORGANISM: Mycobacterium tuberculosis

<400> SEQUENCE: 19

Asp Glu Ala Trp Arg Lys Ala Ile Asp Gly Leu Phe Thr
1               5                   10

<210> SEQ ID NO 20
<211> LENGTH: 103
<212> TYPE: PRT
<213> ORGANISM: Mycobacterium tuberculosis

<400> SEQUENCE: 20

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
                20                  25                  30

Ala Ala Gly Leu Gly Glu Ser Val Ala Ile Thr His Gly Pro Tyr Cys
            35                  40                  45

Ser Gln Phe Asn Asp Thr Leu Asn Val Tyr Leu Thr Ala His Asn Ala
        50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100
```